(12) United States Patent
Heyd et al.

(10) Patent No.: US 11,026,827 B2
(45) Date of Patent: *Jun. 8, 2021

(54) ANKLE FOOT ORTHOSIS (AFO) AND METHOD OF MAKING THE SAME

(71) Applicant: Bracemasters International, LLC, New Berlin, WI (US)

(72) Inventors: Davin T. Heyd, Delavan, WI (US); William D. Falcon, Elkhorn, WI (US)

(73) Assignee: Bracemasters International, LLC, New Berlin, WI (US)

(*) Notice: Subject to any disclaimer, the term of this patent is extended or adjusted under 35 U.S.C. 154(b) by 323 days.

This patent is subject to a terminal disclaimer.

(21) Appl. No.: 15/839,320

(22) Filed: Dec. 12, 2017

(65) Prior Publication Data

US 2018/0098872 A1    Apr. 12, 2018

Related U.S. Application Data

(63) Continuation of application No. 13/837,927, filed on Mar. 15, 2013, now Pat. No. 9,839,547.

(60) Provisional application No. 61/758,421, filed on Jan. 30, 2013.

(51) Int. Cl.
*A61F 5/01* (2006.01)

(52) U.S. Cl.
CPC .......... *A61F 5/0111* (2013.01); *A61F 5/0104* (2013.01); *Y10T 29/49826* (2015.01); *Y10T 156/1028* (2015.01)

(58) Field of Classification Search
CPC .. A61F 5/00; A61F 5/01; A61F 5/0104; A61F 5/0111

USPC ................... 602/23, 27, 60–62, 65; 128/882
See application file for complete search history.

(56) References Cited

U.S. PATENT DOCUMENTS

| | | |
|---|---|---|
| 1,037,441 A | 9/1912 | Collis |
| 1,930,188 A | 10/1930 | Arthur |
| 2,994,322 A | 8/1961 | Cullen et al. |
| 3,333,353 A | 8/1967 | Garcia |
| 3,970,083 A | 7/1976 | Carrigan |
| 4,187,844 A | 2/1980 | Caprio, Jr. |
| D255,384 S | 6/1980 | Finnieston |
| 4,280,488 A | 7/1981 | Polsky et al. |
| 4,489,719 A | 12/1984 | Lapenskie |
| 4,863,779 A * | 9/1989 | Daponte .................. B32B 7/14 428/152 |
| 4,878,505 A | 11/1989 | Thanner |
| 4,998,537 A | 3/1991 | Rau |
| D339,671 S | 9/1993 | Manning |

(Continued)

FOREIGN PATENT DOCUMENTS

WO    2011/113473 A1    9/2011

OTHER PUBLICATIONS

The Richie Brace; Precision Orthotic Lab International; www.precisionorthotic.com/precision/products/richiebrace.htm, Copyright © 2004; 3 pages.

(Continued)

*Primary Examiner* — Keri J Nelson
(74) *Attorney, Agent, or Firm* — SmithAmundsen LLC

(57) ABSTRACT

The present disclosure provides a custom or pre-fabricated ankle foot orthosis providing tri-planar control of the ankle foot structure. The ankle foot orthosis comprises a brace body composed of reinforcement strips and a closure mechanism.

11 Claims, 5 Drawing Sheets

(56) References Cited

U.S. PATENT DOCUMENTS

| | | | |
|---|---|---|---|
| 5,370,604 | A | 12/1994 | Bemardoni |
| 5,456,976 | A | 10/1995 | LaMarca et al. |
| 5,472,414 | A | 12/1995 | Detty |
| 5,501,659 | A | 3/1996 | Morris et al. |
| 5,657,767 | A | 8/1997 | Nelson |
| 5,713,837 | A | 2/1998 | Grim et al. |
| D394,112 | S | 5/1998 | Duback et al. |
| 5,814,002 | A | 9/1998 | Nelson |
| 5,853,380 | A | 12/1998 | Miller |
| 6,024,712 | A | 2/2000 | Iglesias et al. |
| 6,083,184 | A | 7/2000 | Kenosh |
| 6,155,997 | A | 12/2000 | Castro |
| D440,661 | S | 4/2001 | Cionitti |
| 6,212,743 | B1 | 4/2001 | Cohen |
| 6,394,917 | B1 | 5/2002 | Chiappini et al. |
| 6,517,505 | B1 | 2/2003 | Veldman |
| 6,540,705 | B2 | 4/2003 | Norstrem |
| 6,652,474 | B1 | 11/2003 | Quinn et al. |
| 6,663,584 | B2 | 12/2003 | Griesbach, III et al. |
| 6,767,332 | B1 | 7/2004 | Pardue et al. |
| D509,586 | S | 9/2005 | Lee |
| 7,014,621 | B2 | 3/2006 | Nelson |
| 7,018,351 | B1 | 3/2006 | Iglesias et al. |
| D548,846 | S | 8/2007 | Buethorn |
| D552,744 | S | 10/2007 | Verkade et al. |
| D559,988 | S | 1/2008 | Buethorn |
| 7,513,881 | B1 | 4/2009 | Grim et al. |
| 7,651,472 | B2 | 1/2010 | Gaylord et al. |
| 7,691,076 | B2 | 4/2010 | Castro |
| 7,867,180 | B2 | 1/2011 | Cuypers |
| 7,918,811 | B2 | 4/2011 | Lussier et al. |
| 7,950,676 | B2 | 5/2011 | Goldsmith et al. |
| D639,965 | S | 6/2011 | Wehsely-Swiczinsky |
| 7,993,295 | B2 | 8/2011 | Nelson |
| D649,650 | S | 11/2011 | Wehsely-Swiczinsky |
| D682,434 | S | 5/2013 | Heyd et al. |
| 8,512,269 | B1 | 8/2013 | Stano et al. |
| D696,409 | S | 12/2013 | Best et al. |
| D708,344 | S | 7/2014 | Best et al. |
| D722,382 | S | 2/2015 | Lee et al. |
| 9,839,547 | B2 * | 12/2017 | Heyd .................... A61F 5/0111 |
| 2003/0083603 | A1 | 5/2003 | Nelson |
| 2004/0034316 | A1 | 2/2004 | Castro |
| 2005/0096576 | A1 | 5/2005 | Castro |
| 2009/0076428 | A1 | 3/2009 | Kay |
| 2010/0094392 | A1 | 4/2010 | Nguyen et al. |
| 2011/0196276 | A1 | 8/2011 | Kuhn |
| 2014/0188026 | A1 | 7/2014 | Gaylord |
| 2014/0213953 | A1 | 7/2014 | Heyd et al. |
| 2014/0243724 | A1 | 8/2014 | Dodin |
| 2014/0276314 | A1 | 9/2014 | Heyd et al. |

OTHER PUBLICATIONS

Richie Brace—Custom Articulated Ankle Foot Orthosis; www.footcareexpress.com/services/richie_brace_php; Copyright © 2011; 5 pages.

PCT Notification of Transmittal of the International Search Report and the Written Opinion of the International Searching Authority, or the Declaration; PCT International Search Report; PCT Written Opinion of the International Searching Authority relating to International Application No. PCT/US11/58317, dated Feb. 13, 2012 (7 pgs.).

DRAFO DRG; Bracemasters International, LLC; www.bracemasters.com; Apr. 2010; 2 pages.

Need value? quality? results? Think DRAFO; Bracemasters International, LLC; www.bracemasters.com; Sep. 2010; 3 pages.

AS1 Ankle Brace—Active Ankle; www.activeankle.com; at least as early as Dec. 2012; 2 pages.

EZ Lacer Ankle Brace—Active Ankle; www.activeankle.com; at least as early as Dec. 2012; 2 pages.

CF PRO Ankle Brace—Active Innovations; www.activeankle.com; at least as early as Dec. 2012; 2 pages.

PRO MED Ankle Brace—Active Innovations; www.activeankle.com; at least as early as Dec. 2012; 2 pages.

Multi-Phase Ankle Brace—Active Innovations; www.activeankle.com; at least as early as Dec. 2012; 2 pages.

T1 Ankle Brace—Active Ankle; www.activeankle.com; at least as early as Dec. 2012; 2 pages.

T2 Ankle Brace—Active Ankle; www.activeankle.com; at least as early as Dec. 2012; 2 pages.

VOLT Ankle Brace—Active Ankle; www.activeankle.com; at least as early as Dec. 2012; 2 pages.

Johnson, R. et al.; Comparative Study of Ankle Support Devices; Journal of the American Podiatric Medical Association; vol. 84, No. 3; Mar. 1994; available at www.activeankle.com; 1 page.

Parekh, S. et al.; Prophylactic Bracing Decreases Ankle Injuires in Collegiate Female Volleyball Players; University of North Carolina; University of Pennsylvania; at least as early as Dec. 2012; available at www.activeankle.com; 2 pages.

Gehlsen, G. et al.; Ankle Joint Strength, Total Work, and ROM: Comparison Between Prophylactic Devices; Athletic Training JNATA; vol. 26, Spring 1991; available at www.activeankle.com; 4 pages.

Gehlsen, G. et al.; Subtalar Joint Movement During Running on Camber: Comparison Between Prophylactic Devices; Ball State University; at least as early as Dec. 2012; available at www.activeankle.com; 1 page.

Siegler, S. et al.; Heel Pain Control Characteristics of the Active Ankle Brace; Drexel University; at least as early as Dec. 2012; available at www.activeankle.com; 1 page.

Siegler, S. et al.; The Three Dimensional Passive Support Characteristics of Ankle Braces; presented at the 1996 American College of Foot and Ankle Surgeons Meeting and Scientific Seminar; available at www.activeankle.com; 2 pages.

Power Lacer Ankle Brace—Active Ankle; www.activeankle.com; at least as early as Dec. 2012; 2 pages.

The DRAFO DRG—Dynamic Response Gauntlet—Practitioner's Guide; Bracemasters International, LLC; www.bracemasters.com; published after Oct. 28, 2011; 2 pages.

Ossur Form Fit® Ankle Brace; http://www.ossur.com/?PageID=13539; at least as early as Dec. 2012; 2 pages.

DRAFO Caregiver Guide; Bracemasters International, LLC; www.bracemasters.com; Apr. 2011; 2 pages.

DRAFO Selection Guide; Bracemasters International, LLC; www.bracemasters.com; Apr. 2011; 2 pages.

DRAFO Clinical Education Workshop; Bracemasters International, LLC; www.bracemasters.com; Apr. 2011; 2 pages.

DRAFO Introduction; Bracemasters International, LLC; www.bracemasters.com; Apr. 2011; 2 pages.

DRAFO Practitioner Toolbox; Bracemasters International, LLC; www.bracemasters.com; Apr. 2011; 2 pages.

DRAFO Sport—The Ultimate Solution for Athletic Ankle Bracing; Bracemasters International, LLC; www.bracemasters.com; May 2011; 2 pages.

DRAFO Sport advertisement; Bracemasters International, LLC; www.bracemasters.com; May 2011; 1 page.

The DRAFO Difference; Bracemasters International, LLC; www.bracemasters.com; Sep. 2011; 2 pages.

EXCEL Ankle Brace—Active Ankle; www.activeankle.com; at least as early as Dec. 2012; 2 pages.

* cited by examiner

ANKLE FOOT ORTHOSIS (AFO) AND METHOD OF MAKING THE SAME

FIELD

This disclosure relates to providing a custom or prefabricated ankle foot orthosis (AFO). The AFO provides tri-planar control of ankle foot structure inducing stability and control to the hind-foot, mid-foot, and forefoot. This disclosure protects against the results of Posterior Tibial Tendon Dysfunction (PTTD), Ankle Arthritis, and ankle weakness or instability of the ankle-foot structure.

BACKGROUND

Typical ankle foot orthoses use rigid plastic as the primary element of the device with a traditional design that provides less control and less comfort. This traditional design and approach often leads to gait compensation and more limited results for the patient.

The traditional leather ankle gauntlet has been a popular orthosis for nearly 25 years. Though widely accepted for a wide range of patient pathologies, its design features in many cases create problems. These traditional leather gauntlets are nearly impossible to adjust in the field, are difficult to clean, have limited durability, and require significantly more time to manufacture than simplified thermoplastic orthosis designs.

There exists a need in improving upon conventional AFO devices and traditional leather ankle gauntlets. There exists a need for an AFO device that is comfortable and provides needed support, and which can be conveniently fit for a user, including with regard to condition indications, such as Posterior Tibial Tendon Dysfunction (PTTD), ankle arthritis, among others.

SUMMARY

The present disclosure provides an ankle foot orthosis comprising a combination of a closed cell polyethylene foam inner lining bonded to a polyolefin elastomeric material, with one or more key structural thermoplastic components situated between the polyethylene foam inner lining and the outer layer of polyolefin elastomeric material. In an embodiment, a key structural thermoplastic component is wrapped around the posterior half of the proximal edge of the ankle foot orthosis, and a second key structural thermoplastic component is structured as a stirrup-like configuration that extends as a unitary element continuously from the upper medial side to under the mid-foot and back up to the upper lateral side of the orthosis.

Not only does the present disclosure provide an ankle foot orthosis composed of a combination of specific materials varied in stiffness and texture, but it provides a specific relative amount and placement of key structural thermoplastic components to yield an ankle foot orthosis having an improved combination of support, flexibility and comfort that can be tailored to better meet the specific needs of each individual patient.

The ankle foot orthosis is structured to provide tri-planar control of the ankle foot structure inducing stability and control to the hind-foot, mid-foot, and forefoot. In an embodiment, the ankle foot orthosis comprises a brace body comprising a medial side portion, a lateral side portion, a medial front edge of the medial side portion, a lateral front edge of the lateral side portion, a sole portion in a plane at least partially horizontal to the medial and lateral side portions having an arch portion and a heel portion, and a back portion extending from the heel portion to an upper calf portion. In embodiments, the brace body comprises a minimum of three layers including a closed cell polyethylene foam inner layer, a rigid or semi-rigid thermoplastic intermediate layer as key structural thermoplastic components, and a polyolefin elastomeric material as an outer layer. Optionally, an additional material layer can be applied over the surface of the foam inner layer to enhance the texture and provide a soft interface with the foot, for example, a synthetic leather-like material or elastic fabric.

In an embodiment, the ankle foot orthosis comprises a medial stirrup-type reinforcement strip with a first end situated a distance below the proximal edge of the orthosis and extending down along the medial side portion to under the mid-foot, and continuing up the lateral side with a second end situated below the proximal edge of the orthosis. The orthosis further comprises a proximal reinforcement strip beginning on the medial side just below the proximal edge and extending around the posterior side to an end point on the lateral side. The orthosis further includes a closure mechanism positioned on the lateral side end of the proximal reinforcement strip and a closure mechanism positioned on the medial side end of the reinforcement strip. Multiple closure mechanisms can be situated on the lateral anterior edge and the medial anterior edge of the stirrup type reinforcement strip wherein the closure mechanisms are structured and operable to tighten and secure the ankle foot orthosis onto the subject's lower leg and foot.

The present disclosure also provides a method of manufacturing an ankle foot orthosis. In an embodiment, the method comprises the steps of providing a mold of a lower extremity, forming a closed cell polyethylene foam material over the mold, forming at least one key structural thermoplastic component over the closed cell polyethylene foam to bond to the foam as structural reinforcements, forming an outer layer of a polyolefin elastomeric material over the prior two layers on the mold to create a third bonded layer, setting closure mechanisms (e.g., lace loops) into the polyolefin elastomeric outer layer, and removing the mold from the material layers to produce the ankle foot orthosis.

The ankle foot orthosis of the disclosure is an improved alternative to traditional ankle foot orthoses (AFOs), providing a broad range of features and benefits that address the limitations of traditional AFOs and leather ankle gauntlets. The present thermoplastic ankle foot orthosis is hygienic, waterproof, easily cleaned, and is readily adjustable at fitting utilizing a modest heat application. The present device provides more flexible comfort with complete control, and is more durable than traditional ankle foot orthoses. The device has a slim, low profile design that fits inside most shoes. The orthosis of the disclosure provides alternatives to achieving the required level of rigidity and performance that best addresses the needs of each patient's condition covering a broad range of neurological and orthopedic pathologies. The improved AFO provides a soft interface with the patient's foot to enhance comfort and alternatives for closure mechanisms.

BRIEF DESCRIPTION OF THE DRAWINGS

Preferred embodiments of the disclosure are described below with reference to the following accompanying drawings, which are for illustrative purposes only. Throughout the following views, the reference numerals will be used in the drawings, and the same reference numerals will be used

DETAILED DESCRIPTION

Embodiments of the disclosure relate to an ankle foot orthosis (AFO) and methods of making the orthosis. The AFO can be custom-made or pre-fabricated, and provides tri-planar control of the ankle foot structure inducing stability and control to the hind-foot, mid-foot, and forefoot sections. The AFO of the disclosure helps protect against ankle weakness and/or instability of the ankle-foot structure.

Figure 3:
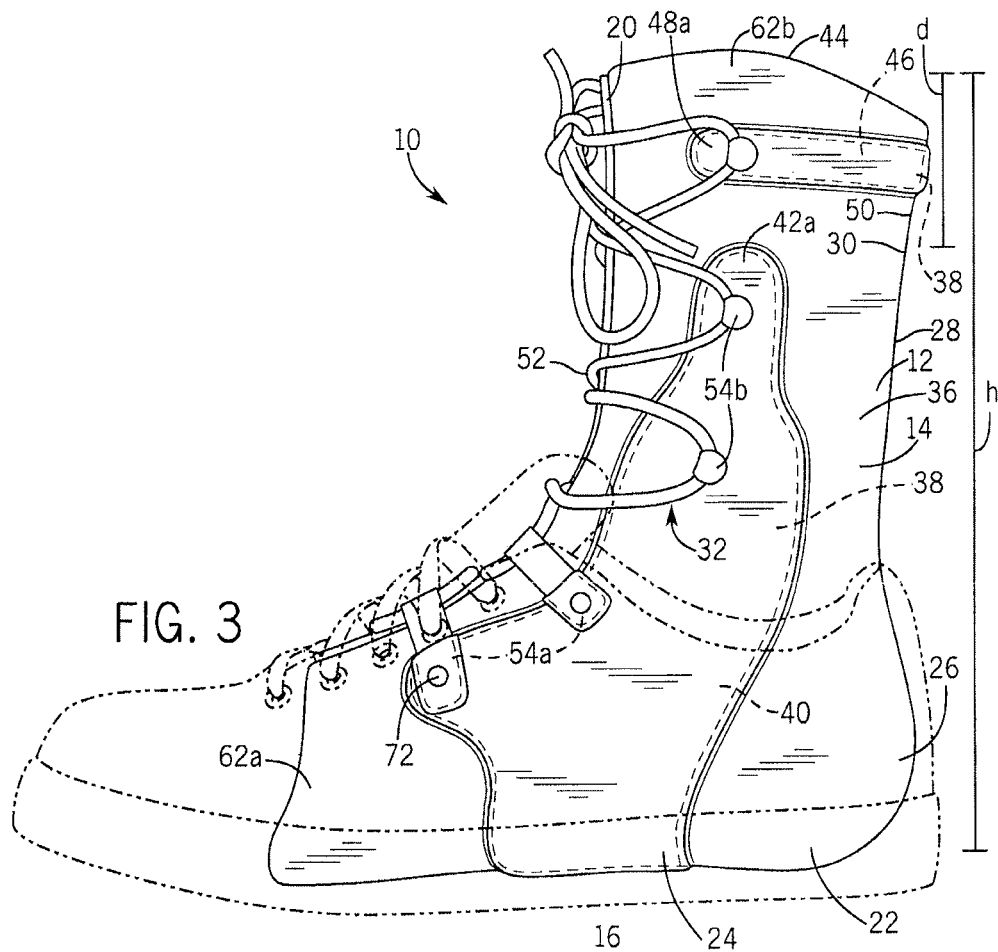
FIG. 3 is a medial side view of the ankle foot orthosis of FIG. 1 positioned inside a shoe (shown in phantom).

An embodiment of an ankle foot orthosis 10 according to the disclosure is described with reference to FIGS. 1, 3 and 4. The orthosis can be used in combination with a standard shoe (shown in phantom in FIG. 3). The orthosis is designed to be worn over a sock and inside the shoe without the need to increase the shoe size to accommodate the orthosis. The orthosis is in the general shape of a toe-less boot.

Figure 1:
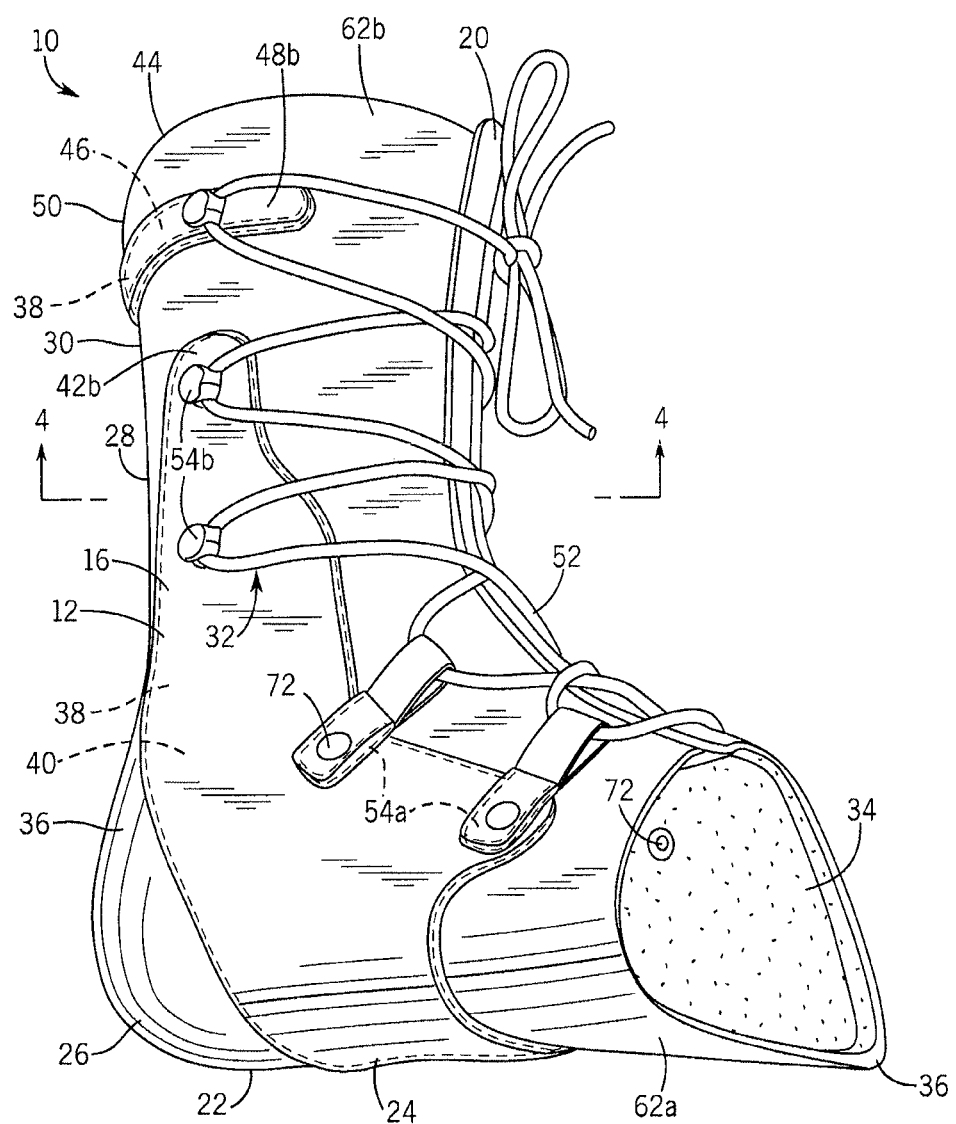
FIG. 1 is a perspective view of an embodiment of an ankle foot orthosis according to the disclosure.
Figure 4:
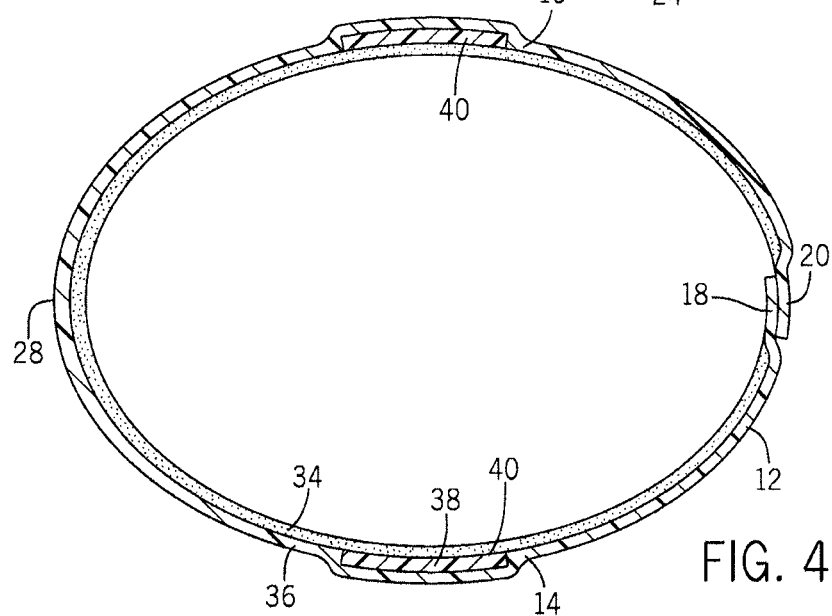
FIG. 4 is a cross-sectional view of the ankle foot orthosis of FIG. 1, taken along line 4-4 of FIG. 1.

Referring to FIGS. 1 and 4, the ankle foot orthosis 10 comprises a brace body 12 having a medial side portion 14, a lateral side portion 16, a medial front edge 18 of the medial side portion 14, a lateral front edge 20 of the lateral side portion 16, a sole portion 22 having an arch portion 24 and a heel portion 26, and a back portion 28 extending from the heel portion 26 to an upper calf portion 30. The sole portion 22 is in a plane at least partially horizontal to the medial and lateral side portions 14, 16 of the brace body 12. As can be seen, at least a portion of the sole portion 22 is at least partially perpendicular to the medial and laterial side portions 14, 16 of the brace body 12. The ankle foot orthosis 10 further includes a closure mechanism 32 to tighten and secure the orthosis to the foot. FIGS. 1 and 3 are lateral and medial side views, respectively, of the ankle foot orthosis 10.

As illustrated, the brace body 12 comprises a laminated structure of at least three material layers including an inner layer 34, a polyolefin elastomeric outer layer 36, and the rigid or semi-rigid key structural components as an intermediate layer 38 between the inner and outer layers 32, 34.

The inner layer 34 is composed of a closed cell polyethylene (PE) foam, which, in embodiments, is at least 1.5 mm thick, preferably at least 3.0 mm thick, up to 4.5 mm thick. Closed cell PE foams are commercially available, for example, under the tradenames Volara® from Sekisui Voltek, LLC (Lawrence, Mass.), and Aliplast from AliMed, Inc. (Dedham, Mass.). Sheets of closed cell polyethylene foam are commercially available.

The outer layer 36 is composed of a rigid or semi-rigid thermoplastic material, preferably a polyolefin elastomeric material having thermoforming capabilities. In embodiments, the outer layer 36 is at least 2.0 mm thick, preferably at least 3.0 mm thick, up to 5.0 mm thick. In an embodiment, the polyolefin elastomeric material is an ethylene-butene copolymer or an ethylene-octene copolymer having a melt index range at 190° C. of less than 0.5 to 30 g/10 min (measured according to ASTM D 1238), a density of 0.857 to 0.910 g/cm$^3$ (measured according to ASTM D 792), a melting range of 36° C. to 104° C., a Shore A Hardness of 56 to 96 (ASTM D 2240), and a flexural modulus from 3 to 110 MPa (measured according to ASTM D 790). In another embodiment, the polyolefin elastomeric material is an ethylene-butene copolymer having a density of 0.885 g/cm$^3$ (measured according to ASTM D 792), a melt index of 2 g/10 min (2.16 kg @ 190° C. measured by ASTM D 1238), a Mooney Viscosity of 13 (ML 1+4 @ 121° C., measured according to ASTM 1646), a Shore A durometer hardness of 82 (measured according to ASTM 2240) and an ultimate tensile strength of 11.2 MPa (508 mm/min measured according to ASTM D 638). Polyolefin elastomers are well known and commercially available, for example, ENGAGE® ethylene/α-olefin copolymers available from The Dow Chemical Company.

The ankle foot orthosis 10 further includes an intermediate layer 38 defined by the key structural components and composed of a thermoplastic, polyolefin elastomeric material that is preferably at least 1.5 mm thick, preferably at least 3.0 mm thick, up to 4.5 mm thick. The key structural thermoplastic components are laminated (or inset) into the orthosis to provide support in target areas without reducing the flexibility of the brace body 12 in other areas. The intermediate layer 38 for the key structural components is preferably stiffer than the thermoplastic material used for the outer layer 36 of the brace body 12. Nonlimiting examples of suitable thermoplastic polyolefin elastomers include polypropylene, polyethylene and modified polyethylene (MPE), which are commercially available from a number of sources.

As shown in FIG. 1, a first key structural component is configured as a medial stirrup-type reinforcement strip 40 in one continuous strip with a first end 42a positioned below the proximal edge 44 of the brace body 12 on the medial side portion 14, preferably at a distance (d) of about one-fourth (or 25%) of the total height (h) of the brace body from the proximal edge 44. The reinforcement strip 40 extends to under the sole portion 22 at the arch portion 24 (at about mid-foot), and continues up the lateral side portion 16 with the second end 42b positioned below the proximal edge 44 of the brace body 12, preferably at a distance (d) of about one-fourth (or 25%) of the total height (h) of the brace body 12 from the proximal edge 44.

In addition, a second key structural component is configured as a proximal reinforcement strip 46 positioned just below the proximal edge 44 of the brace body 12, with a first end 48a positioned on the medial side portion 14 and extending around the posterior side portion 50 with a second end 48b positioned on the lateral side portion 16 of the brace body 12.

The first key structural component (40) (stirrup reinforcement strip 40) hinders the talus range of motion to guard against unwanted tri-planar ankle foot motion. The second key structural component (proximal reinforcement strip 46) provides additional circumferential rigidity and an attachment point for closure mechanisms. When the ankle foot orthosis 10 is fastened on the foot, the first and second key structural components work in conjunction with each other to control tri-planar ankle foot motion.

The closure mechanism 32 may include laces with a series of holes, eyelets, loops or hooks, Velcro® strips (available from Velcro USA, Inc.), elastic closures, cinched straps, zippers, snaps, buttons, hooks, clasps or other suitable fastener. In embodiments, when the closure mechanism 32 is engaged, the medial front edge 18 and the lateral front edge 20 of the brace body overlap, as shown in FIG. 4, such that the brace body does not require a separate tongue element. The overlap can be from 0.125 inches to 1.5 inches (0.32 cm to 3.8 cm), for example, 0.25 inch to 1.0 inch (0.64 cm to 2.5 cm).

As illustrated in FIG. 1, in an embodiment, the closure mechanism 32 is in the form of a lace 52 that cooperates with two or more lace loops 54a positioned on the stirrup reinforcement strip 40 at the distal section 62a of the brace body 12 (or the region that would typically reside inside the shoe) to engage the lace 52 and tighten and secure the ankle foot orthosis 10 onto the subject's foot. Metallic or non-metallic "boot hook" style hardware 54b can be installed in the proximal section 62b of the stirrup-type reinforcement strip 40 (which would typically reside outside the shoe) to engage with the lace 52.

Figure 2:
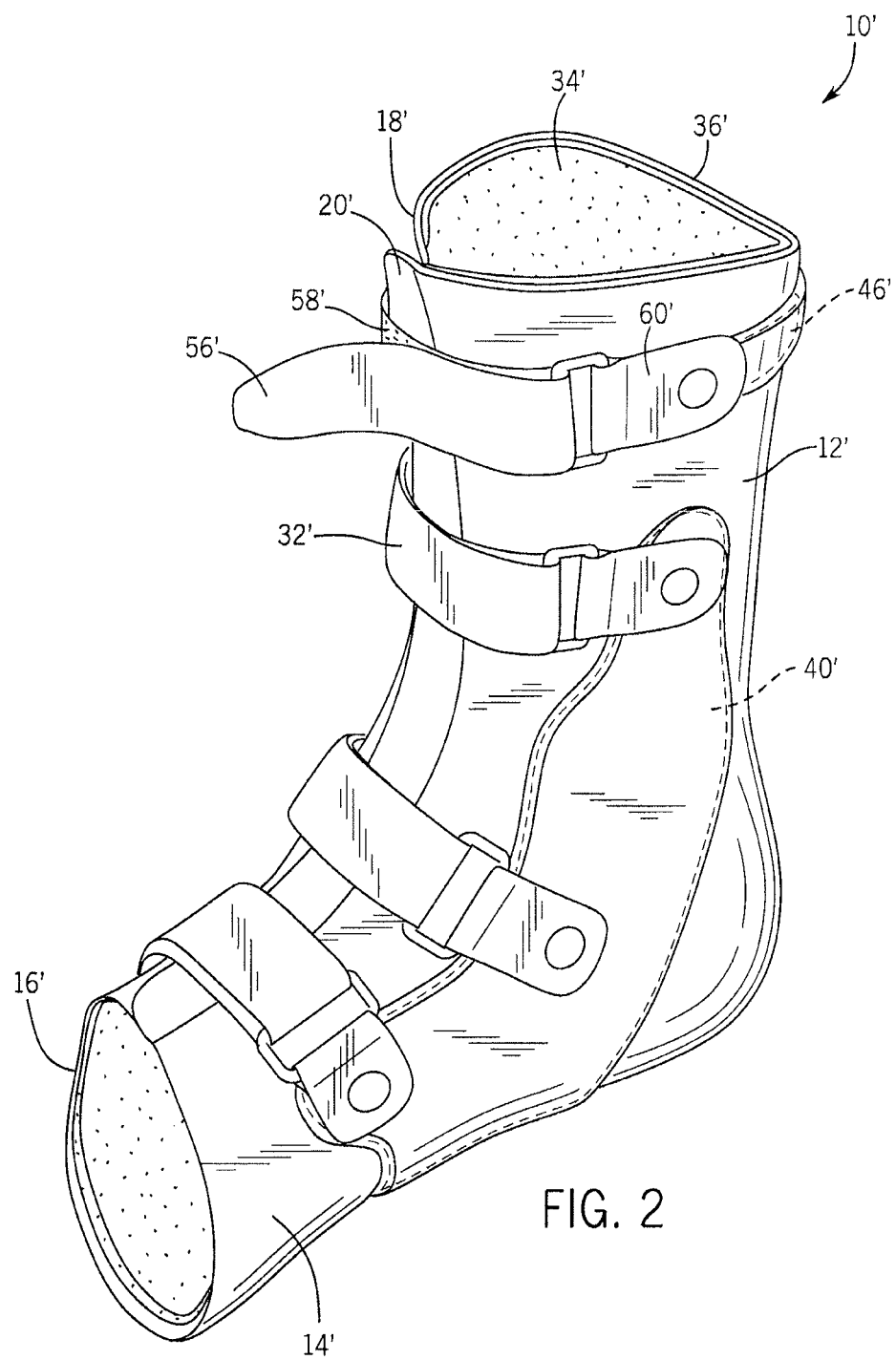
FIG. 2 is a perspective view of another embodiment of an ankle foot orthosis according to the disclosure.

In another embodiment shown in FIG. 2, the closure mechanism 32' is a hook and loop fastening mechanism in the form of an attachment strap 56' as a first Velcro part with a one end secured to the proximal reinforcement strip 46' and the stirrup reinforcement strip 40' on the lateral side portion 16' of the brace body 12', and a loop element 60' secured' to proximal reinforcement strip 46' and the stirrup reinforcement strip 40' on the medial side portion 14'. The second end of the attachment strap 56' is inserted through the loop of the loop element 60', pulled back and attached to a cooperating second Velcro part 58' to tighten the ankle foot orthosis 10' onto the person's foot and ankle.

In some embodiments, the brace body 12 further includes an interface layer (not shown) that is applied over the foam inner layer 34 to enhance and provide a soft interface with the subject's foot. The interface layer can be, for example, a synthetic leather-like material (e.g., Clarino® artificial leather), a synthetic elastic fabric (e.g., Lycra® material), or other soft material.

Optionally, a layer of a synthetic leather-like material (e.g., Clarino® artificial leather) or a synthetic elastic fabric (e.g., Lycra® material) can be applied over the surface of the foam inner layer, or a pre-laminated polyethylene foam with a bonded synthetic layer, to provide an interior interface with the foot to enhance the texture of the soft interface.

Method of Manufacture

Figure 7:
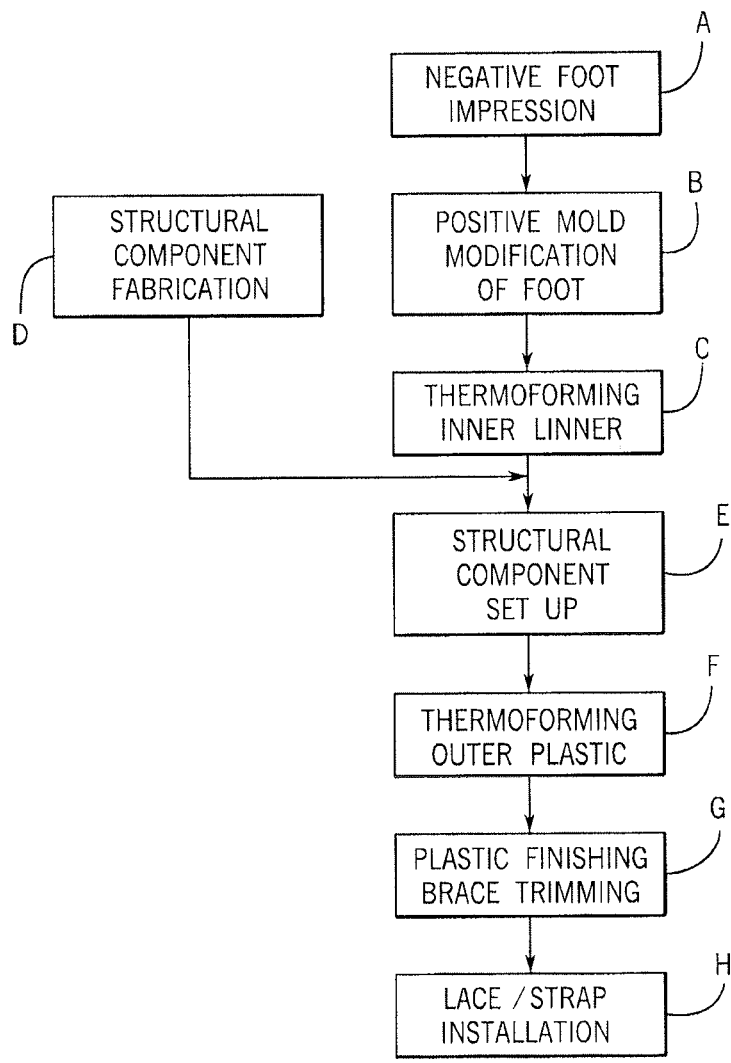
FIG. 7 is a block diagram of an embodiment of a process for making an ankle foot orthosis according to the disclosure.

FIG. 7 provides a process flow diagram of a method of manufacture of an ankle foot orthosis according to the disclosure.

Figure 5:
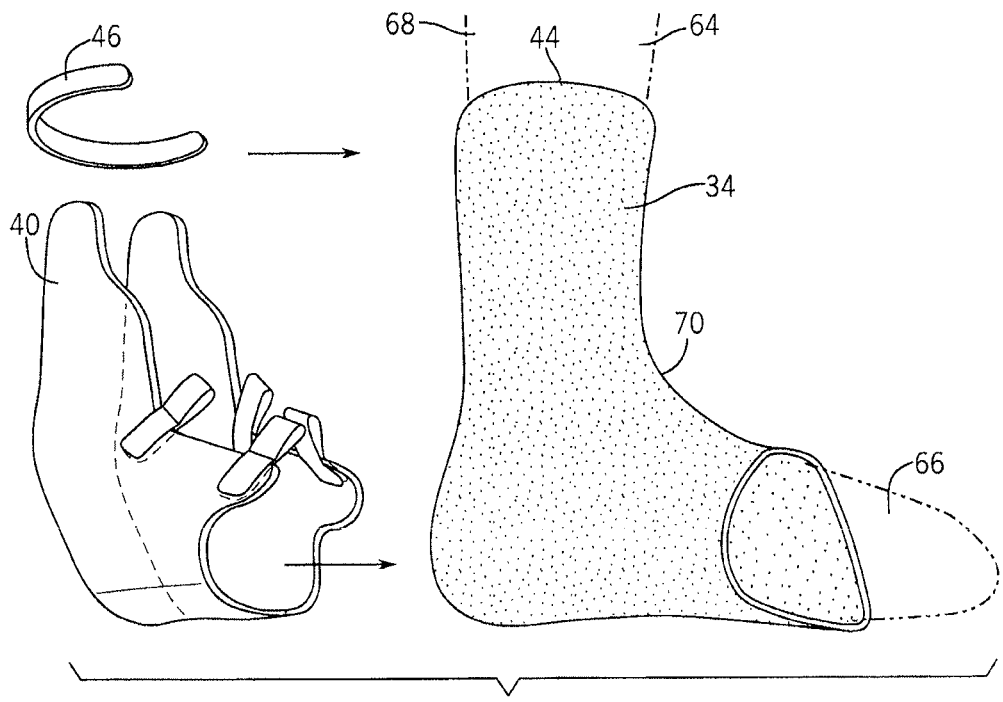
FIG. 5 is an exploded view of the ankle foot orthosis of FIG. 1, showing the inner layer situated on a mold (shown in phantom) and two structural components.

In first steps A and B, a mold 64 (e.g., plaster, wax, metal, wood, epoxy molds) of a patient's lower extremity is provided, as shown in phantom in FIG. 5. The mold 64 may be created from a 3D image or negative cast of the patient's extremity. Alternatively, instead of a mold being made from a patient's scan or cast, the mold may correspond to a pre-fabricated size. Thus, a patient may choose a pre-fabricated standard size that most closely fits their foot size. The correct size is determined by measuring the instep of a patient by placing a flexible tape around the instep and heel with the ankle at 90 degrees. The measurement and patient's shoe size are used to determine the best pre-fabricated size on a sizing chart.

In a typical fabrication approach, the mold 64 to be used for the device being fabricated is mounted in a horizontal, tubular vacuum fixture. In a step C, a closed cell polyethylene foam lining material (for inner layer 34) is heated in sheet form and draped over the mold, from the posterior around to the anterior, thus establishing a straight seam from the toe through the instep and up past the proximal edge of the mold, thus enabling a seal around the tubular vacuum fixture. Vacuum is applied, creating an intimate capture by the closed cell polyethylene lining material 34 of the mold 64, as shown in FIG. 5.

An alternate method incorporates a slightly altered mold geometry, designed to accommodate mounting on a vacuum table, where the closed cell polyethylene foam lining material is mounted in a frame, heated, and brought down over the mounted mold. The closed cell polyethylene foam lining material seals against the table which is connected to a similar vacuum source, thus creating a similar seam and intimate capture of the mounted mold by the closed cell polyethylene lining material.

After the foam liner (inner layer 34) has cooled sufficiently, strategic areas of the closed cell polyethylene liner are cut away from the mold 64 to expose the distal toe 66, the proximal surface 68 of the mold 64, and an anterior strip 70 approximately 1.25-inches (3.2 cm) wide extending from the toe 66 to approximately ½-inch (1.3 cm) from the proximal edge 44. These cut outs provide for sufficient vacuum for subsequent thermoforming steps as well as reducing bulk in the instep region where the finished device will overlap.

In a step D, the key structural thermoplastic components are manufactured using predetermined, standardized sizing and can be stamped out of sheet material using a clicker die press process or similar. The appropriate size of the horizontal/proximal key structural thermoplastic component (proximal reinforcement strip 46) can be determined by taking a measurement from one anterior/posterior midline to the other anterior/posterior midline, at the location to which the component 46 will be mounted as per the fabrication standards established. The appropriate size of the key structural thermoplastic component, the medial stirrup-type reinforcement strip 40, can be determined by placing a thin, flexible, transparent template identical in dimension to the key thermoplastic component on the mold being used for fabrication. The template that fits the fabrication standards established corresponds to the size of the key structural thermoplastic component 40 used for fabrication.

Figure 6:
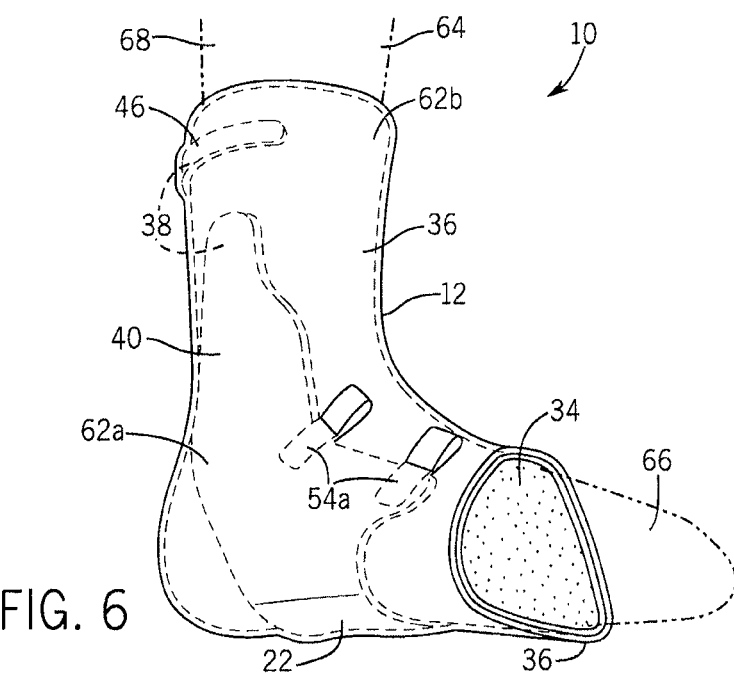
FIG. 6 is a perspective view of the ankle foot orthosis of FIG. 5, in a subsequent process step showing the key structural components on the inner layer and the applied outer layer.

In a step E, both key structural reinforcement components 40, 46 are heated to approximately 225° F. or until they become moldable. The actual temperature required can vary as a function of the thermoplastic material being used for the key structural thermoplastic components. After heating, the components 40, 46 are removed from the oven and, as illustrated in FIGS. 5 and 6, placed, nearly simultaneously, onto the closed cell polyethylene liner material (inner layer 34), in locations outlined by the fabrication standard. A heat resistant plastic or silicone bag is placed over the entire mold assembly and sealed to the vacuum pipe, at which point vacuum is applied, thus creating an intimate relationship between the bag, the thermoplastic key structural reinforcement components 40, 46 and the mold 64 and closed cell polyethylene liner 34 assembly. Vacuum is applied until the thermoplastic components 40, 46 have cooled to a non-moldable temperature, at which point the vacuum bag is removed from the assembly. During this process, the key structural reinforcement thermoplastic components 40, 46 will have bonded permanently to the closed cell polyethylene lining material 34. The bases of the lace loops 54a are placed on the distal section 62a (or the region that would typically reside inside the shoe) of the medial stirrup-type reinforcement strip 40. Alternatively, Velcro fasteners can be placed on the exterior of the brace body 12 on the distal section 62a. In an embodiment, the bases of the lace loops 54a are heat welded or ultrasonic welded together.

In a next step F, the polyolefin elastomeric material to form the outer layer 36 is thermoformed over the assembly, typically using a method nearly identical to the process used for the closed cell polyethylene lining material 34. During thermoforming, the polyolefin elastomeric material outer layer 36 is heated to a temperature from 225° F. to 250° F. and placed over the mold 64, the key structural thermoplastic components 40, 46, and the lace loops 54a to produce the brace body 12. In an embodiment, after the polyolefin elastomeric material for the outer layer 36 is draped over the mold 64 from the posterior around to the anterior thus establishing a straight seam from the region of the toe 66, through the instep (sole portion 22) and up past the proximal edge 68 of the mold 64, a vacuum is used to seal the polyolefin elastomeric material outer layer 36 over the mold, the key structural thermoplastic components 40, 46, and the lace loops 54a. The vacuum can be maintained until the polyolefin elastomeric material outer layer 36 returns to room temperature. The mold 64 is then removed once the polyolefin elastomeric material outer layer 36 has cooled to room temperature to produce the ankle foot orthotic 10.

In a next step G, finishing and trimming of the plastic layers of the brace body is performed.

In a next step H, a cut is made in the polyolefin elastomeric material outer layer 36 across the width of the distal base of a lace loop 54a just dorsal to the stirrup-type reinforcement strip 40, from which the lace loop 54a is pulled through to partially expose the lace loop 54a for future lacing. Fasteners 72 are added to further secure the base of the lace loops 54a, outer layer 36, the stirrup-type reinforcement strip 40, and the foam inner layer 34 together. Metallic or non-metallic "boot hook" style hardware 54b can be installed in the proximal section 62b of the medial stirrup-type reinforcement strip 40 (which would typically reside outside the shoe), approximate one-half of the orthosis 10, through the outer layer 36 of polyolefin elastomeric material, the closed cell polyethylene liner material (inner layer) 34, and the first and second key structural thermoplastic components 40, 46. Laces can be added through the lace loops 54a and boot hooks 54b.

In an embodiment, the height of the anterior and dorsal surfaces of the mold are such that the medial front edge 18 and the lateral front edge 20 may be overlapped when the ankle foot orthosis is tightened by the closing mechanism 32, as illustrated in FIGS. 1 and 2.

Additionally, in an embodiment, the closed cell polyethylene lining material (inner layer 34), the key structural reinforcement components 40, 46, and the base of the lace loops 54a are laminated in the brace body 12 such that a layer of a synthetic fabric (e.g., Clarino or Lycra) is first placed on the mold, or use a pre-laminated foam with a bonded synthetic layer, followed by the placement of the polyethylene foam inner lining material (34), the key structural reinforcement components 40, 46, and the base of the lace loops 54a. Then the outer layer 36 of polyolefin elastomeric material is placed over the reinforcement strips 40, 46 and lace loops 54a thereby encapsulating the key structural reinforcement components and lace loops in the brace body. Other closure mechanisms besides lace loops and laces are contemplated and considered within the scope of the disclosure.

It is specifically intended that the present disclosure not be limited to the embodiments and illustrations contained herein, but include modified forms of those embodiments including portions of the embodiments and combinations of elements of different embodiments as come within the scope of the following claim.

What is claimed is:

1. An ankle foot orthosis, comprising:
   a brace body comprising a first polyolefin elastomeric material, the brace body comprising:
      a back portion;
      a medial side portion having a medial front edge;
      a lateral side portion having a lateral front edge;
      a sole portion;
      a proximal edge;
   a first reinforcement strip of a second polyolefin elastomeric material, the first reinforcement strip being a single medial stirrup-type strip having a first end situated on the medial side portion below the proximal edge and extending as a continuous strip along the medial side portion, under the sole portion and along the lateral side portion, to a second end situated on the lateral side portion below the proximal edge, to hinder talus range of motion and guard against unwanted tri-planar ankle foot motion;
   the medial front edge and the lateral front edge being configured for an overlapping arrangement; and
   a closure mechanism to tighten the ankle foot orthosis on a foot;
   wherein the brace body comprises a closed cell foam inner lining bonded to an outer layer comprising the first polyolefin elastomeric material, with the first reinforcement strip situated between the inner lining and the outer layer;
   wherein the first polyolefin elastomeric material is an ethylene-butene copolymer or an ethylene-octene copolymer, and the second polyolefin elastomeric material is selected from the group consisting of polypropylene, polyethylene, and modified polyethylene (MPE); and
   wherein the first polyolefin elastomeric material has a melt index of less than 0.5 30 g/10 minutes (measured according to ASTM D 1238), a density of 0.857 to 0.910 g/cc (measured according to ASTM D 792), a melting range of 36° C. to 140° C., a Shore A hardness of 56 to 96 (measured according to ASTM D 2240), and a flexural modulus of from 3 to 110 MPa (measured according to ASTM D 790).

2. The ankle foot orthosis of claim 1, further comprising a second reinforcement strip positioned below the proximal edge with a first end situated on the medial side portion and extending along the back portion with a second end situated on the lateral side portion.

3. The ankle foot orthosis of claim 2, wherein the second reinforcement strip is positioned in at least a partially parallel orientation to the proximal edge.

4. The ankle foot orthosis of claim 2, wherein the first and second reinforcement strips comprise a polyolefin elastomeric material.

5. The ankle foot orthosis of claim 1, wherein the closure mechanism comprises laces, hooks, loops, elastic, fasteners, or a combination thereof.

6. The ankle foot orthosis of claim 1, wherein the closure mechanism comprises laces and lace loops.

7. The ankle foot orthosis of claim 6, wherein the lace loops have a base in contact with the first reinforcement strip.

8. The ankle foot orthosis of claim 6, further comprising a second reinforcement strip positioned below the proximal edge with a first end situated on the medial side portion and extending along the back portion with a second end situated on the lateral side portion, wherein the closure mechanism further comprises boot hooks mounted on the first reinforcement strip, the second reinforcement strip, or both.

9. The ankle foot orthosis of claim 1, being structured for insertion into a shoe.

10. The ankle foot orthosis of claim 1, where the sole portion is in a plane at least partially horizontal to the medial and lateral side portions.

11. The ankle foot orthosis of claim 1, wherein the sole portion is at least partially perpendicular to at least a portion of the medial side portion, at least a portion of the lateral side portion, or both.

\* \* \* \* \*